US011523861B2

(12) United States Patent
Sims et al.

(10) Patent No.: US 11,523,861 B2
(45) Date of Patent: Dec. 13, 2022

(54) METHODS FOR MANUFACTURING A JAW ASSEMBLY FOR AN ELECTROSURGICAL FORCEPS

(71) Applicant: COVIDIEN LP, Mansfield, MA (US)

(72) Inventors: Grant T. Sims, Boulder, CO (US); Kelley D. Goodman, Erie, CO (US); Craig V. Krastins, Arvada, CO (US); Robert F. Mccullough, Jr., Boulder, CO (US); Daniel W. Mercier, Erie, CO (US); Jennifer L. Rich, Parker, CO (US)

(73) Assignee: COVIDIEN LP, Mansfield, MA (US)

( * ) Notice: Subject to any disclaimer, the term of this patent is extended or adjusted under 35 U.S.C. 154(b) by 803 days.

(21) Appl. No.: 16/362,162

(22) Filed: Mar. 22, 2019

(65) Prior Publication Data

US 2020/0297405 A1 Sep. 24, 2020

(51) Int. Cl.
*A61B 18/14* (2006.01)
*A61B 17/00* (2006.01)
*A61B 18/00* (2006.01)

(52) U.S. Cl.
CPC .......... *A61B 18/1445* (2013.01); *A61B 18/14* (2013.01); *A61B 18/1442* (2013.01);
(Continued)

(58) Field of Classification Search
CPC . A61B 18/1445; A61B 18/14; A61B 18/1442; A61B 2017/00526; A61B 2018/00083; A61B 2018/0091
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 Y 9/2009
CN 202086577 U 12/2011
(Continued)

OTHER PUBLICATIONS

Barbara Levy, "Use of a New Vessel Ligation Device During Vaginal Hysterectomy" FIGO 2000, Washington, D.C.. (1 page).
(Continued)

*Primary Examiner* — Peter Dungba Vo
*Assistant Examiner* — Azm A Parvez
(74) *Attorney, Agent, or Firm* — Carter, DeLuca & Farrell LLP (57) ABSTRACT

A method of assembling a jaw member of an electrosurgical forceps includes aligning in vertical registration an electrically conductive seal plate, an insulative spacer and a jaw support. The method further includes stacking the seal plate atop the insulative spacer and the jaw support such that a flange depending from the seal plate seats within a corresponding cavity defined within a flange depending from the insulative spacer which, in turn, seats within a cavity defined within the jaw support. The method further includes mechanically securing the seal plate, insulative spacer and jaw support to one another and securing a jaw housing to surround the jaw support, the insulative spacer and the seal plate.

11 Claims, 6 Drawing Sheets

(52) U.S. Cl.
CPC ............... *A61B 2017/00526* (2013.01); *A61B 2018/00083* (2013.01); *A61B 2018/0091* (2013.01)

(58) Field of Classification Search
USPC .... 29/825; 606/41, 2, 42, 46, 32, 48, 34, 51
See application file for complete search history.

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| 4,763,669 A | 8/1988 | Jaeger | |
| D298,353 S | 11/1988 | Manno | |
| D299,413 S | 1/1989 | DeCarolis | |
| 5,100,420 A | 3/1992 | Green et al. | |
| 5,258,001 A | 11/1993 | Corman | |
| D343,453 S | 1/1994 | Noda | |
| 5,304,203 A | 4/1994 | El-Mallawany et al. | |
| D348,930 S | 7/1994 | Olson | |
| D349,341 S | 8/1994 | Lichtman et al. | |
| 5,344,424 A | 9/1994 | Roberts et al. | |
| D354,564 S | 1/1995 | Medema | |
| D358,887 S | 5/1995 | Feinberg | |
| 5,540,685 A | 7/1996 | Parins et al. | |
| 5,578,052 A | 11/1996 | Koros et al. | |
| 5,611,808 A | 3/1997 | Hossain et al. | |
| 5,618,294 A | 4/1997 | Aust et al. | |
| D384,413 S | 9/1997 | Zlock et al. | |
| 5,665,100 A | 9/1997 | Yoon | |
| 5,752,644 A | 5/1998 | Bolanos et al. | |
| H1745 H | 8/1998 | Paraschac | |
| 5,814,043 A | 9/1998 | Shapeton | |
| D402,028 S | 12/1998 | Grimm et al. | |
| D408,018 S | 4/1999 | McNaughton | |
| 5,913,874 A | 6/1999 | Berns et al. | |
| 5,960,544 A | 10/1999 | Beyers | |
| D416,089 S | 11/1999 | Barton et al. | |
| 6,050,996 A | 4/2000 | Schmaltz et al. | |
| D424,694 S | 5/2000 | Tetzlaff et al. | |
| D425,201 S | 5/2000 | Tetzlaff et al. | |
| H1904 H | 10/2000 | Yates et al. | |
| 6,293,954 B1 | 9/2001 | Fogarty et al. | |
| D449,886 S | 10/2001 | Tetzlaff et al. | |
| 6,329,778 B1 | 12/2001 | Culp et al. | |
| 6,334,861 B1 | 1/2002 | Chandler et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| 6,406,485 B1 | 6/2002 | Hossain et al. | |
| H2037 H | 7/2002 | Yates et al. | |
| 6,464,704 B2 | 10/2002 | Schmaltz et al. | |
| D465,281 S | 11/2002 | Lang | |
| D466,209 S | 11/2002 | Bon | |
| 6,511,480 B1 | 1/2003 | Tetzlaff et al. | |
| 6,673,092 B1 | 1/2004 | Bacher | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| 7,118,570 B2 | 10/2006 | Tetzlaff et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| 7,329,257 B2 | 2/2008 | Kanehira et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,431,730 B2 | 10/2008 | Viola | |
| D582,038 S | 12/2008 | Swoyer et al. | |
| 7,641,653 B2 | 1/2010 | Dalla Betta et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| 7,854,185 B2 | 12/2010 | Zhang et al. | |
| D630,324 S | 1/2011 | Reschke | |
| 7,896,878 B2 | 3/2011 | Johnson et al. | |
| D649,249 S | 11/2011 | Guerra | |
| D649,643 S | 11/2011 | Allen, IV et al. | |
| 8,147,489 B2 | 4/2012 | Moses et al. | |
| D661,394 S | 6/2012 | Romero et al. | |
| 8,298,233 B2 | 10/2012 | Mueller | |
| D670,808 S | 11/2012 | Moua et al. | |
| 8,366,709 B2 | 2/2013 | Schechter et al. | |
| 8,394,096 B2 | 3/2013 | Moses et al. | |
| D680,220 S | 4/2013 | Rachlin | |
| 8,409,246 B2 | 4/2013 | Kerr et al. | |
| 8,409,247 B2 | 4/2013 | Garrison et al. | |
| 8,425,504 B2 | 4/2013 | Orton et al. | |
| 8,425,511 B2 | 4/2013 | Olson | |
| 8,430,877 B2 | 4/2013 | Kerr et al. | |
| 8,439,913 B2 | 5/2013 | Horner et al. | |
| 8,469,716 B2 | 6/2013 | Fedotov et al. | |
| 8,469,991 B2 | 6/2013 | Kerr | |
| 8,469,992 B2 | 6/2013 | Roy et al. | |
| 8,480,671 B2 | 7/2013 | Mueller | |
| 8,491,624 B2 | 7/2013 | Kerr et al. | |
| 8,491,625 B2 | 7/2013 | Horner | |
| 8,491,626 B2 | 7/2013 | Roy et al. | |
| 8,512,336 B2 | 8/2013 | Couture | |
| 8,540,749 B2 | 9/2013 | Garrison et al. | |
| 8,551,091 B2 | 10/2013 | Couture et al. | |
| 8,556,929 B2 | 10/2013 | Harper et al. | |
| 8,568,397 B2 | 10/2013 | Horner et al. | |
| 8,568,408 B2 | 10/2013 | Townsend et al. | |
| 8,585,736 B2 | 11/2013 | Horner et al. | |
| 8,591,510 B2 | 11/2013 | Allen, IV et al. | |
| 8,597,295 B2 | 12/2013 | Kerr | |
| 8,623,018 B2 | 1/2014 | Horner et al. | |
| 8,628,557 B2 | 1/2014 | Collings et al. | |
| 8,641,712 B2 | 2/2014 | Couture | |
| 8,647,343 B2 | 2/2014 | Chojin et al. | |
| 8,652,135 B2 | 2/2014 | Nau, Jr. | |
| 8,663,222 B2 | 3/2014 | Anderson et al. | |
| 8,672,939 B2 | 3/2014 | Garrison | |
| 8,679,098 B2 | 3/2014 | Hart | |
| 8,685,009 B2 | 4/2014 | Chernov et al. | |
| 8,685,021 B2 | 4/2014 | Chernov et al. | |
| 8,685,056 B2 | 4/2014 | Evans et al. | |
| 8,702,737 B2 | 4/2014 | Chojin et al. | |
| 8,702,749 B2 | 4/2014 | Twomey | |
| 8,734,445 B2 | 5/2014 | Johnson et al. | |
| 8,740,898 B2 | 6/2014 | Chojin et al. | |
| 8,745,840 B2 | 6/2014 | Hempstead et al. | |
| 8,747,434 B2 | 6/2014 | Larson et al. | |
| 8,756,785 B2 | 6/2014 | Allen, IV et al. | |
| 8,784,418 B2 | 7/2014 | Romero | |
| 8,795,269 B2 | 8/2014 | Garrison | |
| 8,808,288 B2 | 8/2014 | Reschke | |
| 8,814,864 B2 | 8/2014 | Gilbert | |
| 8,840,639 B2 | 9/2014 | Gerhardt, Jr. et al. | |
| 8,845,636 B2 | 9/2014 | Allen, IV et al. | |
| 8,852,185 B2 | 10/2014 | Twomey | |
| 8,852,228 B2 | 10/2014 | Nau, Jr. | |
| 8,858,553 B2 | 10/2014 | Chojin | |
| 8,864,753 B2 | 10/2014 | Nau, Jr. et al. | |
| 8,864,795 B2 | 10/2014 | Kerr et al. | |
| 8,887,373 B2 | 11/2014 | Brandt et al. | |

(56) References Cited

U.S. PATENT DOCUMENTS

| | | |
|---|---|---|
| 8,888,771 B2 | 11/2014 | Twomey |
| 8,888,775 B2 | 11/2014 | Nau, Jr. et al. |
| 8,898,888 B2 | 12/2014 | Brandt et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 9,028,484 B2 | 5/2015 | Craig |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,084,608 B2 | 7/2015 | Larson et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,211,657 B2 | 12/2015 | Ackley et al. |
| 9,265,568 B2 | 2/2016 | Chernov et al. |
| 9,333,002 B2 | 5/2016 | Garrison |
| 9,381,059 B2 | 7/2016 | Garrison |
| 9,456,870 B2 | 10/2016 | Chernov et al. |
| 9,498,278 B2 | 11/2016 | Couture et al. |
| 9,498,279 B2 | 11/2016 | Artale et al. |
| 9,504,519 B2 | 11/2016 | Kerr et al. |
| 9,585,709 B2 | 3/2017 | Krapohl |
| 9,615,877 B2 | 4/2017 | Tyrrell et al. |
| 9,655,672 B2 | 5/2017 | Artale et al. |
| 2003/0018332 A1 | 1/2003 | Schmaltz et al. |
| 2003/0109875 A1 | 6/2003 | Tetzlaff et al. |
| 2003/0199869 A1 | 10/2003 | Johnson et al. |
| 2003/0220637 A1 | 11/2003 | Truckai et al. |
| 2003/0229344 A1 | 12/2003 | Dycus et al. |
| 2004/0092927 A1 | 5/2004 | Podhajsky et al. |
| 2005/0070889 A1 | 3/2005 | Nobis et al. |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2005/0159745 A1 | 7/2005 | Truckai et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0179499 A1 | 8/2007 | Garrison |
| 2007/0260241 A1 | 11/2007 | Dalla Betta et al. |
| 2008/0215048 A1 | 9/2008 | Hafner et al. |
| 2009/0131934 A1 | 5/2009 | Odom et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2009/0302090 A1 | 12/2009 | Shah |
| 2009/0308909 A1 | 12/2009 | Nalagatla et al. |
| 2010/0016857 A1 | 1/2010 | McKenna et al. |
| 2010/0130977 A1 | 5/2010 | Garrison et al. |
| 2010/0179545 A1 | 7/2010 | Twomey et al. |
| 2010/0179547 A1 | 7/2010 | Cunningham et al. |
| 2010/0228250 A1 | 9/2010 | Brogna |
| 2010/0274244 A1 | 10/2010 | Heard |
| 2010/0292691 A1 | 11/2010 | Brogna |
| 2010/0305567 A1 | 12/2010 | Swanson |
| 2011/0054469 A1 | 3/2011 | Kappus et al. |
| 2011/0060314 A1 | 3/2011 | Wallace et al. |
| 2011/0060356 A1 | 3/2011 | Reschke et al. |
| 2011/0072638 A1 | 3/2011 | Brandt et al. |
| 2011/0087218 A1 | 4/2011 | Boudreaux et al. |
| 2011/0218530 A1 | 9/2011 | Reschke |
| 2011/0238065 A1 | 9/2011 | Hunt et al. |
| 2011/0238067 A1 | 9/2011 | Moses et al. |
| 2011/0257680 A1 | 10/2011 | Reschke et al. |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0184988 A1 | 7/2012 | Twomey et al. |
| 2012/0184989 A1 | 7/2012 | Twomey |
| 2012/0184990 A1 | 7/2012 | Twomey |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1* | 10/2012 | Garrison ............ A61B 18/1442 606/51 |
| 2012/0265241 A1 | 10/2012 | Hart et al. |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1* | 1/2013 | Sims ................... A61B 17/285 29/434 |
| 2013/0018411 A1 | 1/2013 | Collings et al. |
| 2013/0022495 A1 | 1/2013 | Allen, IV et al. |
| 2013/0030432 A1 | 1/2013 | Garrison et al. |
| 2013/0041370 A1 | 2/2013 | Unger |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0178852 A1 | 7/2013 | Allen, IV et al. |
| 2013/0185922 A1 | 7/2013 | Twomey et al. |
| 2013/0190753 A1 | 7/2013 | Garrison et al. |
| 2013/0190760 A1 | 7/2013 | Allen, IV et al. |
| 2013/0197503 A1 | 8/2013 | Orszulak |
| 2013/0226177 A1 | 8/2013 | Brandt et al. |
| 2014/0221994 A1 | 8/2014 | Reschke |
| 2014/0221995 A1 | 8/2014 | Guerra et al. |
| 2014/0221999 A1 | 8/2014 | Cunningham et al. |

(56) References Cited

U.S. PATENT DOCUMENTS

| | | |
|---|---|---|
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | Mccullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | Mckenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0066076 A1 | 3/2015 | Kerr et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2015/0297288 A1* | 10/2015 | Joseph ............... A61B 18/1445 29/854 |
| 2016/0157925 A1 | 6/2016 | Artale et al. |
| 2016/0175031 A1 | 6/2016 | Boudreaux |
| 2017/0128120 A1 | 5/2017 | Cho et al. |

FOREIGN PATENT DOCUMENTS

| | | |
|---|---|---|
| CN | 102525639 A | 7/2012 |
| DE | 2415263 A1 | 10/1975 |
| DE | 02514501 A1 | 10/1976 |
| DE | 2627679 A1 | 1/1977 |
| DE | 03423356 A1 | 1/1986 |
| DE | 3612646 A1 | 4/1987 |
| DE | 3627221 A1 | 2/1988 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| EP | 1532932 A1 | 5/2005 |
| EP | 2301468 A1 | 3/2011 |
| EP | 2353535 A1 | 8/2011 |
| EP | 2436327 A1 | 4/2012 |
| EP | 2436330 A1 | 4/2012 |
| EP | 2529681 A1 | 12/2012 |
| EP | 3072467 A1 | 9/2016 |
| JP | 61501068 | 9/1984 |
| JP | 6502328 | 3/1992 |
| JP | 55106 | 1/1993 |
| JP | H0540112 A | 2/1993 |
| JP | 6121797 A | 5/1994 |
| JP | 6285078 A | 10/1994 |
| JP | 6511401 | 12/1994 |
| JP | H06343644 A | 12/1994 |
| JP | H07265328 A | 10/1995 |
| JP | H0856955 A | 3/1996 |
| JP | 08252263 A | 10/1996 |
| JP | H08289895 | 11/1996 |
| JP | H08317934 | 12/1996 |
| JP | H08317936 | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | H1024051 A | 1/1998 |
| JP | H10155798 A | 6/1998 |
| JP | 1147149 | 2/1999 |
| JP | H1147150 A | 2/1999 |
| JP | H1170124 A | 3/1999 |
| JP | H11169381 | 6/1999 |
| JP | H11192238 | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029355 A | 2/2001 |
| JP | 2001029356 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| SU | 401367 A1 | 10/1973 |
| WO | 9400059 | 1/1994 |
| WO | 9923933 A2 | 5/1999 |
| WO | 0024330 | 5/2000 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 02080786 A1 | 10/2002 |
| WO | 02080793 A1 | 10/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |
| WO | 2013009758 A2 | 1/2013 |
| WO | 2013022928 A1 | 2/2013 |
| WO | 2013134044 A1 | 9/2013 |
| WO | 2015017991 A1 | 2/2015 |

OTHER PUBLICATIONS

Vallfors et al., Automatically Controlled Bipolar Electrocoagulation—"COA-COMP", Neurosurg. Rev. (1984), pp. 187-190.

(56) References Cited

OTHER PUBLICATIONS

Examination Report No. 1 issued in corresponding Australian Application No. 2018201752 dated Aug. 8, 2018, 10 pages.
Extended European Search Report issued in corresponding application No. 18171773.7 dated Oct. 8, 2018, 7 pages.
Canadian Office Action issued in Canadian Application No. 2,997,771 dated Jan. 4, 2019, 3 pages.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz, abandoned.
U.S. Appl. No. 09/591,328, filed Jun. 9, 2000, Thomas P. Ryan.
U.S. Appl. No. 12/336,970, filed Dec. 17, 2008, Paul R. Sremeich, abandoned.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Herman et al., "Laparoscopic Intestinal Resection With the LigaSure Vessel Sealing System: A Case Report" Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.
Heniford et al. "Initial Results with an Electrothermal Bipolar Vessel Sealer" Surgical Endoscopy (2000) 15:799-801. (4 pages).
"Reducing Needlestick Injuries in the Operating Room" Sales/Product Literature 2001. (1 page).
Levy et al., "Update on Hysterectomy—New Technologies and Techniques" OBG Management, Feb. 2003. (15 pages).

\* cited by examiner

METHODS FOR MANUFACTURING A JAW ASSEMBLY FOR AN ELECTROSURGICAL FORCEPS

BACKGROUND

The present disclosure relates to electrosurgical instruments and, more particularly, to electrosurgical forceps for grasping, treating, and/or dividing tissue and methods for manufacturing the same.

TECHNICAL FIELD

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, during assembly, an electrically conductive tissue sealing plate of each jaw member is mounted atop a jaw housing and is secured in place utilizing various manufacturing techniques.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about +/−10 degrees from true parallel and true perpendicular.

Aspects according to the present invention include a method of assembling a jaw member of an electrosurgical forceps, including: aligning in vertical registration an electrically conductive seal plate, an insulative spacer and a jaw support; stacking the seal plate atop the insulative spacer and the jaw support such that a flange depending from the seal plate seats within a corresponding cavity defined within a flange depending from the insulative spacer which, in turn, seats within a cavity defined within the jaw support; mechanically securing the seal plate, insulative spacer and jaw support to one another; and securing a jaw housing to surround the jaw support, the insulative spacer and the seal plate (or at least a portion thereof).

In aspects according to the present disclosure, one or more rivets or screws mechanically secure the seal plate, insulative spacer and jaw support to one another. In other aspects, the method includes feeding an electrical connection from the seal plate, through the insulative spacer and jaw structure and back to an electrical source.

In aspects according to the present disclosure, the jaw housing is secured by overmolding the jaw housing to surround the jaw support, the insulative spacer and the seal plate. In yet other aspects, the seal plate includes a peripheral edge that mechanically engages a corresponding lip of the jaw housing to secure the jaw housing to the seal plate.

In aspects according to the present disclosure, the seal plate includes a peripheral edge that mechanically engages the jaw housing during the overmolding process to secure the jaw housing to the seal plate. In still other aspects, the jaw housing is made from an insulative material. Yet in other aspects, the jaw support is made from metal.

Aspects according to the present invention include a method of assembling a jaw member of an electrosurgical forceps, including: aligning in vertical registration an electrically conductive seal plate, an insulative spacer and a jaw support; seating the seal plate atop the insulative spacer and the jaw support such that a flange depending from the seal plate depends generally perpendicular to the seal plate and is spaced relative to the insulative spacer in an initial, pre-overmold configuration; and overmolding a jaw housing to surround the seal plate, insulative spacer and jaw support wherein the overmolding forces the flange of the seal plate to mechanically engage the insulative spacer in a second, after-overmold configuration.

In aspects according to the present disclosure, the depending flange surrounds the periphery of the seal plate. In other aspects, the depending flange mechanically engages the insulative spacer on either side thereof to secure the seal plate thereon.

In still other aspects, the jaw housing is made from an insulative material. Yet in other aspects, the jaw support is made from metal.

Aspects according to the present invention include a method of assembling a jaw member of an electrosurgical forceps, including: aligning an electrically conductive seal plate having a mesh-like material engaged to a bottom surface thereof and a jaw support, the mesh-like material spacing the seal plate and the jaw support relative to one another; overmolding a first material to fill the mesh-like material and secure the seal plate and the jaw support in spaced relation relative to one another; and overmolding a jaw housing to surround the seal plate, mesh-like material and jaw support.

In aspects according to the present disclosure, the mesh-like material is bonded, welded, integrally associated with or mechanically engaged to the seal plate. In other aspects, the jaw housing is made from an insulative material. Yet in other aspects, the jaw support is made from metal.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1A:
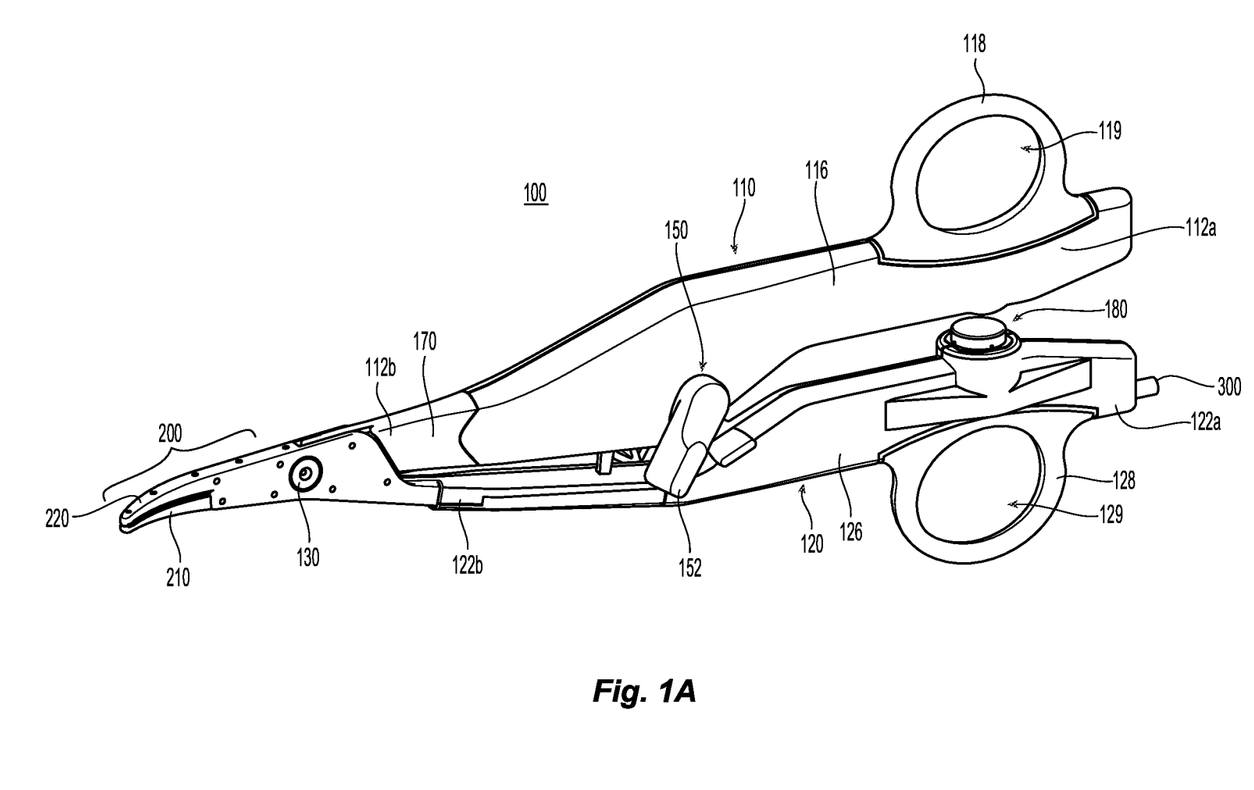
FIG. 1A is a side, perspective view of an electrosurgical forceps provided in accordance with aspects of the present disclosure.
Figure 1B:
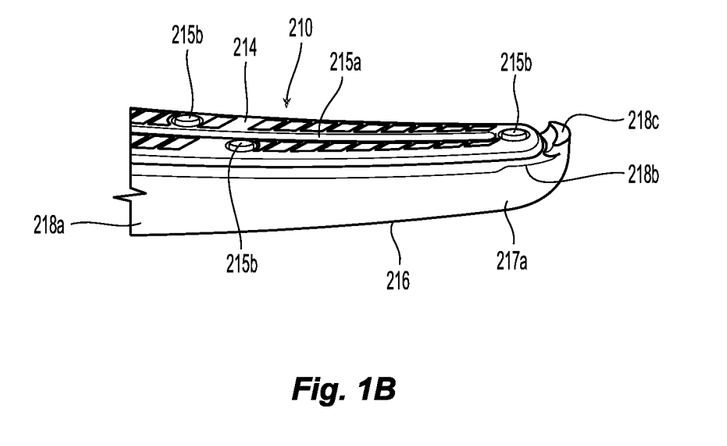
FIG. 1B is an enlarged, side, perspective view of a distal portion of the jaw member of FIG. 1A.

Referring generally to FIGS. 1A and 1B, a forceps 100 provided in accordance with the present disclosure includes first and second shaft members 110, 120 each having a proximal end portion 112a, 122a and a distal end portion 112b, 122b. Although the figures and the below description relate to an open forceps, the present disclosure is equally applicable to a laparoscopic forceps, however, the electrical and mechanical connections may differ depending upon a particular purpose.

An end effector assembly 200 of forceps 100 includes first and second jaw members 210, 220 extending from distal end portions 112b, 122b of shaft members 110, 120, respectively. Forceps 100 further includes a pivot member 130 pivotably coupling first and second shaft members 110, 120 with one another, a knife 140 (not shown), a knife deployment mechanism 150 for selectively deploying the knife relative to end effector assembly 200, a knife lockout 170 for inhibiting deployment of knife prior to sufficient closure of jaw members 210, 220, and a switch assembly 180 for enabling the selective supply of electrosurgical energy to end effector assembly 100. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

Continuing with reference to FIGS. 1A and 1B, each shaft member 110, 120 includes an outer housing 116, 126 surrounding at least a portion of the respective shaft members 110, 120 and a handle 118, 128 engaged with the respective outer housing 116, 126 towards proximal end portions 112a, 122a of shaft members 110, 120, respectively. Outer housings 116, 126 enclose and/or operably support the internal components disposed within shaft members 110, 120. More specifically, as detailed below, outer housing 116 of shaft member 110 encloses and supports at least knife deployment mechanism 150, and lockout 170, while outer housing 126 of shaft member 120 receives electrosurgical cable 300 and encloses and supports switch assembly 180, and the lead wires (not shown) of electrosurgical cable 300. Handles 118, 128 are engaged with outer housings 116, 126 towards proximal end portions 112a, 112b of shaft members 110, 120 and extend outwardly from shaft members 110, 120. Handles 118, 128 define finger holes 119, 129 configured to facilitate grasping and manipulating shaft members 110, 120.

Referring to FIG. 1B, jaw member 210 includes an electrically-conductive, tissue-contacting plate 214 that is secured atop a spacer 233 and a jaw support structure 235 surrounded by an insulative housing 216. Tissue-contacting plate 214 defines a longitudinally-extending knife channel 215a extending at least partially therethrough and may include one or more stop members 215b disposed thereon and electrically isolated therefrom. Insulative housing 216 of jaw member 210 is overmolded or otherwise secured about a portion of jaw support 212 and tissue-contacting plate 214 of shaft member 110. Other manufacturing techniques are explained in detail below with respect to FIGS. 2A-6C. An electrical lead 310 (see FIGS. 6A-6C) is configured to electrically couple to tissue-contacting plate 214 and insulative housing 216 is configured to protect and facilitate routing of the electrical lead 310 from shaft member 120, around pivot 130, and distally therefrom to electrically couple to tissue-contacting plate 214.

A distal portion 217a of insulative housing 216 of jaw member 210 extends about the periphery of tissue-contacting plate 214 and defines a main section 218a, a raised section 218b, and a beak section 218c. Main section 218a of distal portion 217a of insulative housing 216 extends on either side of tissue-contacting plate 214 and is offset relative thereto such that tissue-contacting plate 214 is raised relative to main section 218a. Raised section 218b of distal portion 217a of insulative housing 216 extends distally from main section 218a on either side of tissue-contacting plate 214 and is still recessed relative to tissue-contacting plate 214 but is closer to being co-planar with tissue-contacting plate 214 as compared to main section 218a. Beak section 218c of distal portion 217a of insulative housing 216 is disposed distally of tissue-contacting plate 214 and extends to or beyond tissue-contacting plate 214. Beak section 218c inhibits tissue from entering the area between jaw members 210, 220 of end effector assembly 200 when end effector assembly 200 is disposed in the closed position and utilized for blunt dissection.

Figure 2:
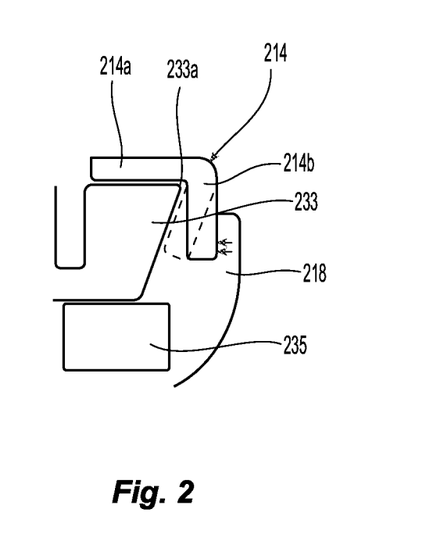
FIG. 2 is a schematic cross section of a jaw member in accordance with one aspect of the present disclosure showing a seal plate being deformed against a jaw spacer as part of a manufacturing technique for securing the seal plate atop the jaw member.

Turning to FIG. 2, one method of securing seal plate 214 atop the spacer and jaw support 235 is shown. More particularly, during an initial manufacturing step, the seal plate 214 is positioned atop the spacer 233 which rests atop the jaw support 235. The seal plate 214 includes a tissue engaging surface 214a and downwardly extending flange 214b that extends at least partially along the spacer 233 once seated atop the spacer 233. During the initial manufacturing step and once seal plate 214 is seated atop spacer 233, the flange 214b is spaced from spacer 233. Insulative housing 216 is then overmolded over the spacer 233, jaw support 235 and a portion of the flange 214b of seal plate 214 to capture and secure the seal plate 214 atop the spacer 233 and jaw support 235. During the overmolding process, the flange 214b of the seal plate 214 is deformed (e.g., bent) against an outer peripheral surface 233a of the spacer 233 to secure the sealing plate 214 thereto (See phantom in FIG. 2). In embodiments, spacer 233 may include a geometry (dovetail, angled face, etc.) to mechanically engage the flange 214b.

Figure 3A:
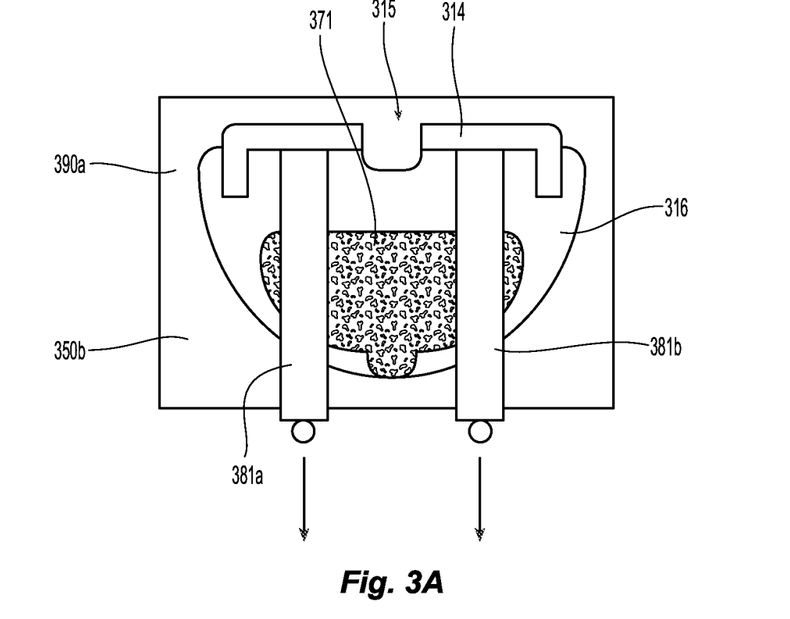
FIG. 3A is a schematic cross section of another jaw member in accordance with another aspect of the present disclosure showing a seal plate being held in place prior to an overmolding process.
Figure 3B:
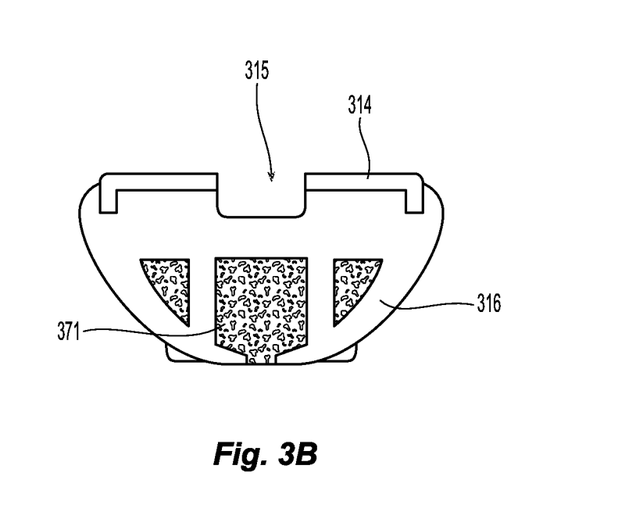
FIG. 3B is a schematic cross section of the jaw member of FIG. 3A showing the seal plate secured in place after the overmolding process.

FIGS. 3A-3B illustrate another method of securing a seal plate 314 atop an insulative spacer 316 and jaw support 371. More particularly, during an initial manufacturing step, the seal plate 314 is held in spaced relation relative to the jaw support 371 by retention posts or cores 381a and 381b and placed within a mold that includes top and bottom halves 390a, 390b. An insulative spacer 316 is then overmolded to fill the space between the seal plate 314 and the jaw support 371 to capture and secure the seal plate 314 atop the jaw support 371 in a single step molding process. In embodiments, the seal plate 314 may include a geometry (dovetail, angled face, etc.) to mechanically engage the insulative spacer 316. In embodiments, the retention posts or cores 381a and 381b are removed during the overmold process.

Figure 4A:
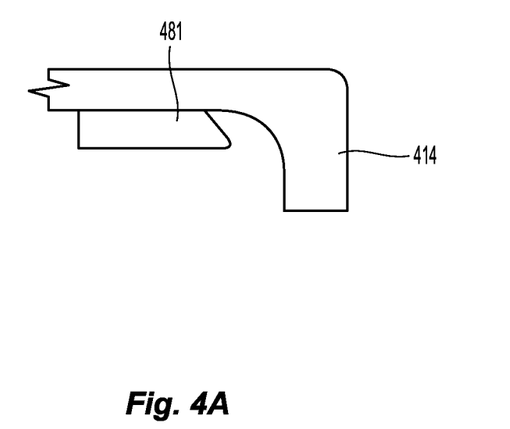
FIG. 4A is a schematic cross section of another jaw member in accordance with another aspect of the present disclosure showing a seal plate being held in place by a mesh-like material prior to an overmolding process.
Figure 4B:
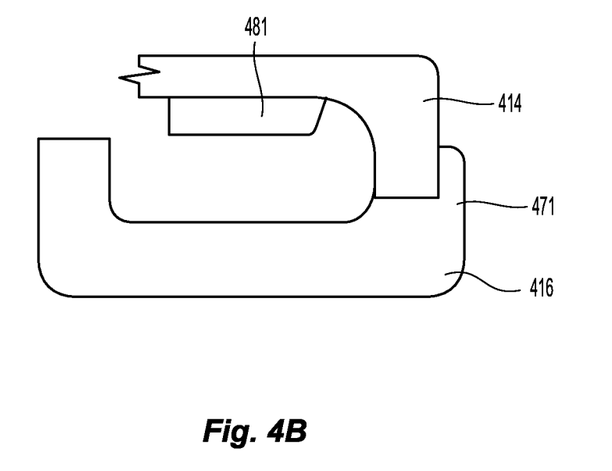
FIG. 4B is a schematic cross section of the jaw member of FIG. 4A showing the seal plate secured in place after the overmolding process.

FIGS. 4A-4B illustrate another method of securing a seal plate 414 atop an insulative spacer and jaw support 471. More particularly, during an initial manufacturing step, the seal plate 414 is held in spaced relation relative to the jaw support 471 by a mesh-like material 481. A first overmolding process fills the mesh-like material 481 (or other materials using holes and counterbores) and secures seal plate 414 in spaced relation atop the jaw support 471. An insulative housing 416 is then overmolded to surround the jaw support 471 and secure the seal plate 414 atop the jaw support 471. In embodiments, the seal plate 314 may include a geometry (dovetail, angled face, etc.) to mechanically engage the insulative housing 416. The mesh-like material 481 may be metal and welded, bonded or crimped to the underside of the seal plate 414. The mesh-like material 481 may also be a polymer material or the same material as the insulative housing 416.

Figure 5:
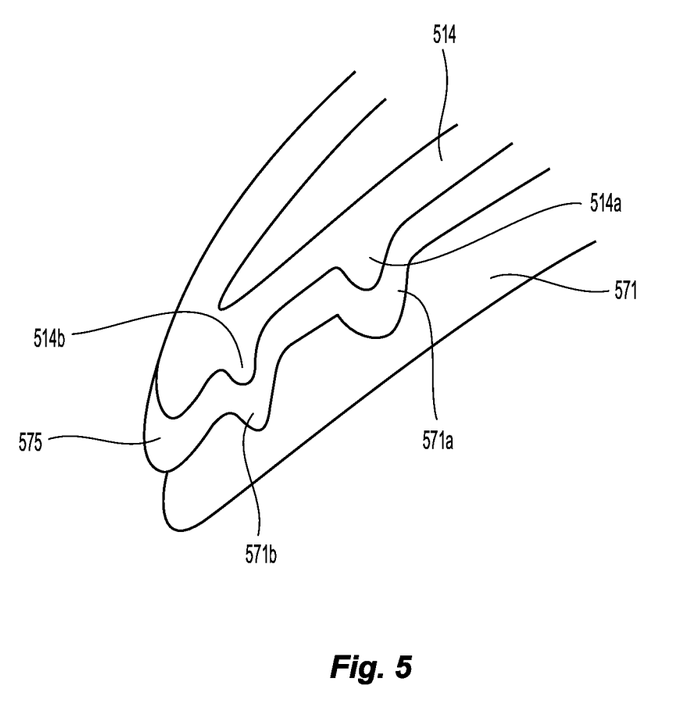
FIG. 5 is a schematic cross section of another jaw member in accordance with another aspect of the present disclosure showing a seal plate including a series of mechanical interfaces engaging a complementary series of mechanical interfaces of a jaw structure to secure the seal plate thereto.

FIG. 5 illustrates yet another method of securing a seal plate 514 atop an insulative spacer 575 and jaw support 571. More particularly, during an initial manufacturing step, the seal plate 514 is registered in spaced relation relative to the jaw support 571 prior to overmolding. A series of mechanical interfaces (flanges, scallops, dove-tails, tabs, etc.) 514a, 514b are aligned in registry with a corresponding series of mechanical interfaces (grooves, slots, depressions) 571a, 571b defined within the jaw support 571. An insulative spacer 575 is then overmolded to fill the space between the seal plate 514 and the jaw support 571 to capture and secure the seal plate 514 atop the jaw support 571 in a single step molding process.

Figure 6A:
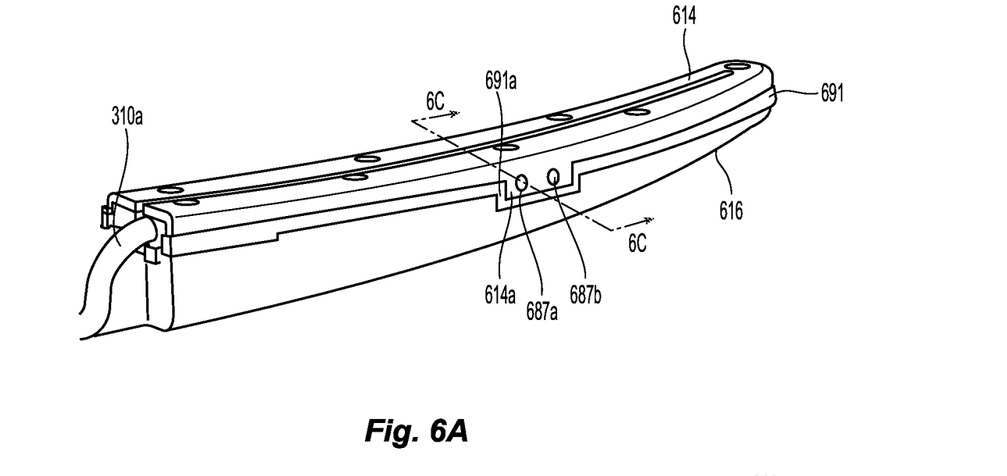
FIG. 6A is an enlarged, side, perspective view of a distal portion of a jaw member in accordance with another aspect of the present disclosure showing a seal plate including a mechanical interface engaging a complementary mechanical interface of a jaw structure and a complementary mechanical interface of a spacer to secure the seal plate the jaw structure.
Figure 6B:
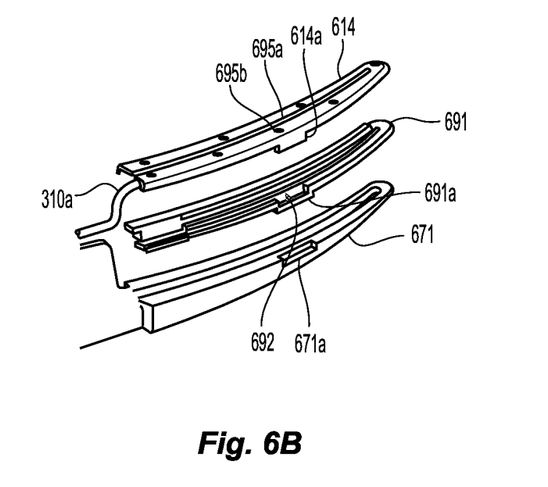
FIG. 6B is an exploded, perspective view of the jaw member of FIG. 6A.
Figure 6C:
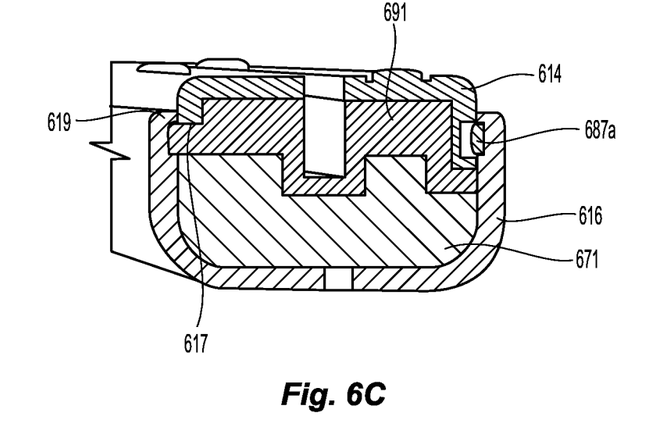
FIG. 6C is a side, perspective cross section of the jaw member of FIG. 6A with an insulative coating surrounding the jaw structure.

FIGS. 6A-6C illustrates yet another method of securing a seal plate 614 atop an insulative spacer 691 and jaw support 671. The jaw support 671 may be metallic. More particularly, during an initial manufacturing step, the seal plate 614, insulative spacer 691 and jaw support 671 are aligned in registry atop one another. One or more scallops or flanges 614a are configured to depend from seal plate 614 along a peripheral edge thereof. A corresponding cavity 692 is defined within a flange 691a of insulative spacer 691 and is dimensioned to seat flange 614a therein. Flange 691a is, in turn, dimensioned to seat within a corresponding cavity 671a defined within jaw support 671. During assembly, flanges 614a, 691a and cavity 671a are aligned and assembled atop one another (See FIGS. 6B and 6A). One or more rivets or screws 687a, 687b may be utilized to secure the seal plate 614 atop the insulative spacer 691 and jaw support 671 after assembly. Flange 614a may include one or more holes 695a, 695b (See FIG. 6B) defined therein to facilitate this purpose. An electrical connection (e.g., wire 310a) may be fed from the seal plate 614, through the insulative spacer 691 and jaw structure 671 and back to an electrical source during the assembly process (See FIG. 6B). Once the seal plate 614, insulative spacer 691 and jaw support 671 are assembled, an outer jaw housing 616 may be overmolded (or otherwise secured) to surround the jaw support 671, insulative spacer 691 and seal plate 614 (or a portion thereof) in a molding process. The outer jaw housing 616 may be made from an insulative material. As can be appreciated, when utilizing rivets or screws, additional overmolding steps may be eliminated.

In embodiments, the seal plate 614 may include a peripheral edge 617 disposed therearound that is dimensioned to mechanically engage (snap-fit, friction fit, compression fit, etc.) a corresponding lip 619 of the jaw housing 616 to secure the jaw housing 616 to the seal plate 614. If the jaw housing 616 is overmolded to surround the seal plate 614, insulative spacer 691 and jaw support 671, the peripheral edge 617 of the seal plate 614 may be dimensioned to mechanically engages the jaw housing 616 during the overmolding process to secure the jaw housing 616 to the seal plate 614.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of assembling a jaw member of an electrosurgical forceps, comprising:
aligning in vertical registration an electrically conductive seal plate, an insulative spacer and a jaw support, the electrically conductive seal plate including a peripheral edge having a flange extending vertically relative to the rest of the peripheral edge of the electrically conductive seal plate;
aligning in vertical registration the flange of the electrically conductive seal plate with a cavity formed by a flange extending vertically from a peripheral edge of the insulative spacer;
aligning in vertical registration the flange of the insulative spacer with a cavity formed in a peripheral edge of the jaw support;
stacking the seal plate atop the insulative spacer and the jaw support such that the flange of the seal plate seats within the cavity of the insulative spacer which, in turn, seats within the cavity of the jaw support;
mechanically securing the seal plate, insulative spacer and jaw support to one another; and
securing a jaw housing to surround the jaw support, the insulative spacer and at least a portion of the seal plate.

2. The method of assembling a jaw member of an electrosurgical forceps according to claim 1, wherein at least one rivet or screw mechanically secures the seal plate, insulative spacer and jaw support to one another.

3. The method of assembling a jaw member of an electrosurgical forceps according to claim 1, further comprising feeding an electrical connection from the seal plate, through the insulative spacer and jaw structure and back to an electrical source.

4. The method of assembling a jaw member of an electrosurgical forceps according to claim 1, wherein the jaw housing is secured by overmolding the jaw housing to surround the jaw support, the insulative spacer and at least a portion of the seal plate.

5. The method of assembling a jaw member of an electrosurgical forceps according to claim 1, wherein the seal plate includes a peripheral edge that mechanically engages a corresponding lip of the jaw housing to secure the jaw housing to the seal plate.

6. The method of assembling a jaw member of an electrosurgical forceps according to claim 4, wherein the seal plate includes a peripheral edge that mechanically engages the jaw housing during overmolding to secure the jaw housing to the seal plate.

7. The method of assembling a jaw member of an electrosurgical forceps according to claim 1, wherein the jaw housing is made from an insulative material.

8. The method of assembling a jaw member of an electrosurgical forceps according to claim 1, wherein the jaw support is made from metal.

9. The method of assembling a jaw member of an electrosurgical forceps according to claim 1, wherein the flange of the insulative spacer extends vertically relative to the rest of the peripheral edge of the insulative spacer.

10. The method of assembling a jaw member of an electrosurgical forceps according to claim 1, wherein the cavity of the jaw support is recessed relative to the rest of the peripheral edge of the jaw support.

11. The method of assembling a jaw member of an electrosurgical forceps according to claim 1, wherein the cavity formed by the flange of the insulative spacer is recessed relative to the rest of the peripheral edge of the insulative spacer.

* * * * *